United States Patent [19]

Hori et al.

[11] Patent Number: 4,578,988

[45] Date of Patent: Apr. 1, 1986

[54] METHOD FOR MEASURING CHANGES IN A PHYSICAL PROPERTY OF LIQUID AND SEMISOLID MATERIALS

[75] Inventors: Tomoshige Hori; Masatoshi Kako, both of Sayama; Hiromichi Hayashi, Tokyo, all of Japan

[73] Assignee: Snow Brand Milk Products Co., Ltd., Japan

[21] Appl. No.: 693,012

[22] Filed: Jan. 18, 1985

[30] Foreign Application Priority Data

Jan. 20, 1984 [JP] Japan .................................. 59-7334

[51] Int. Cl.$^4$ ...................... G01N 11/00; G01N 25/18
[52] U.S. Cl. ............................................ 73/54; 374/43
[58] Field of Search ........................ 73/54; 374/43, 44

[56] References Cited

U.S. PATENT DOCUMENTS 4,501,145  2/1985  Boegli et al. ..................... 374/44 X

OTHER PUBLICATIONS

Parsons, Jr. et al., *Measurement of Properties of Liquids and Gasses Using a Hot-Wire Technique*, in Rev. Sci. Instr. 49(10), pp. 1460-1463, Oct. 1978.

Nagasaka et al., *Simultaneous Measurement of the Thermal Conductivity and Diffusivity of Liquids by Transient Hot-Wire Method*, in Rev. Sci. Instr. 52(2), pp. 229-232, Feb. 1981.

Kitazawa et al., *Measurement of Thermal Conductivity of Liquids by Transient Hot-Wire Method*, in Jour. of JSME, 24(188), pp. 374-379, Feb. 1981.

*Primary Examiner*—Stewart J. Levy
*Assistant Examiner*—Joseph W. Roskos
*Attorney, Agent, or Firm*—McGlew and Tuttle

[57] ABSTRACT

Disclosed is a method for measuring changes in a physical property of a liquid or semisolid material which comprises placing a thin metal wire in the material; passing an electric current through the thin metal wire in such a way that the temperature difference between the material and the thin metal wire is kept constant; measuring the intensity of the electric current; and calculating the heat transfer coefficient at the surface of the thin metal wire on the basis of the measured intensity of the electric current and thereby detecting changes in a physical property of the material. This method makes it possible to detect, for example, changes in the coefficient of kinematic viscosity of a food having the form of a gel or changes in the condition of thrombus formation in a blood vessel.

6 Claims, 5 Drawing Figures

METHOD FOR MEASURING CHANGES IN A PHYSICAL PROPERTY OF LIQUID AND SEMISOLID MATERIALS

BACKGROUND OF THE INVENTION

1. Field of the Invention

This invention relates to a method for continuously measuring changes with time in a physical property of various liquid and semisolid materials without destroying the original state thereof.

2. Description of the Prior Art

Conventionally, a physical property (e.g., coefficient of viscosity) of a liquid or semisolid material has been measured by rotating a cylinder or a sphere in a sample to be tested or by allowing a sphere to fall freely in the sample.

However, these methods have the inherent disadvantage that, where the sample is in a semisolid form, the sample itself is destroyed in consequence of the measurement. For example, in the case of a processed food whose viscosity changes in the course of processing, the greatest care must be taken in controlling the behavior of its viscosity, whether the foods may be liquid or semisolid. But, in measuring its coefficient of viscosity for the above-described controlling purpose, the internal structure of the processed food itself may often be destroyed. Accordingly, the physical property (e.g., coefficient of viscosity) determined by analysis of the measured results obtained with destruction of its internal structure will be useless for predicting changes in viscosity of the processed food which does not undergo any destruction or is destroyed at a quite different rate.

Moreover, where a physical property of materials (such as biological tissue and the like) whose properties change with time, the above-described methods involving destruction of the sample can only evaluate the physical property at a specific point of time and cannot predict its changes with time by any possibility. That is, changes in a physical property of such materials must be measured in real time and continuously.

In order to measure the degree of coagulation of raw milk in in the manufacture of cheese and yogurt without deforming the curd by the application of an external force or breaking it down, the present inventor previously developed a method for detecting changes in the degree of coagulation of milk which comprises placing a thin metal wire in milk being coagulated, passing an electric current intermittently or continuously through the thin metal wire, and measuring the increase in temperature of the thin metal wire with the lapse of time (Japanese Patent Application No. 92079/'83).

Although this method is useful in measuring the degree of coagulation of milk, it is of no practical use in measuring changes in a physical property of systems undergoing a wide range of changes or systems very sensitive to temperature (e.g., biological systems), because the temperature rise caused by the electric current flowing through the aforesaid thin metal wire may result in thermal destruction. Even when this method is used to measure the degree of coagulation of milk, the separation of whey from the curd may result because of the excessive heating caused by the electric current flowing through the thin metal wire.

SUMMARY OF THE INVENTION

The present invention has been made in view of the above-described existing state of the art and it is therefore an object of the invention to provide a method for the real-time and continuous measurement of changes in a physical property of a wide variety of liquid and semisolid materials including not only milk but also biological systems as described above, without destroying the original state of these materials mechanically or thermally.

In accordance with the essential feature of the present invention, changes in a physical property of a liquid or semisolid material are measured by placing a thin metal wire in the material; passing an electric current continuously or intermittently through the thin metal wire in such a way that the temperature difference between the material and the thin metal wire is kept constant; measuring the intensity of the electric current; and calculating the heat transfer coefficient at the surface of the thin metal wire on the basis of the measured intensity of the electric current and thereby detecting changes in a physical property of the material.

BRIEF DESCRIPTION OF THE DRAWINGS

In FIG. 1, reference numerals 5 and 6 indicate a thin metal wire and a stainless steel cylinder, respectively. In FIG. 3, reference numerals 7, 8 and 9 indicate a sample, a thermostatically controlled bath and a sensor, respectively. In FIGS. 4 and 5, reference numerals 1, 2, 3 and 4 indicate an artificial blood vessel, a thin platinum wire, blood and a thrombus, respectively.

DETAILED DESCRIPTION OF THE INVENTION

Figure 1:
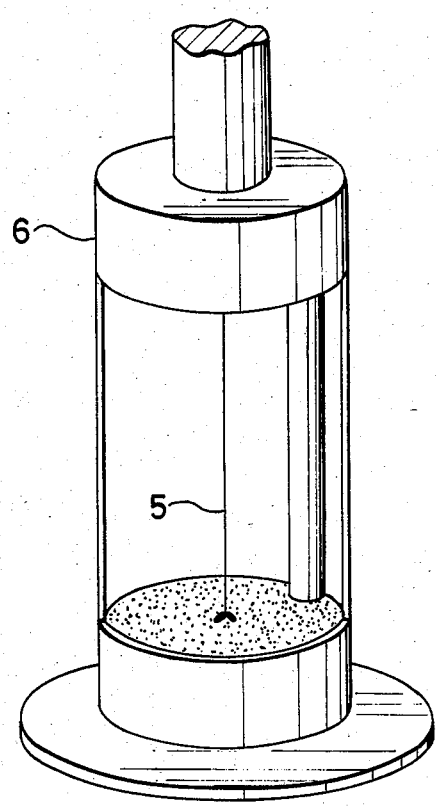
FIG. 1 is a perspective view of a sensor incorporating a thin metal wire for use in the present invention.

The materials to which the present method for measuring changes in a physical property can be applied include, for example, gel-like foods such as cheese, yogurt, bean curd, jelly, pudding, etc.; and biological fluids such as blood, etc. In addition, the method of the present method is also useful in examining the degree of solidification of an adhesive resin (such as an epoxy resin) injected into a place which cannot be observed from outside, the whipped condition of cream, the whipped and solidified condition of ice cream mix, the occurrence of solidification of cream in its transfer pipes, and the like.

The method of the present invention is based on the principle that a physical property, such as the coefficient of kinematic viscosity $v$ (m$^2$/s) defined as the ratio of the coefficient of viscosity $\eta$ (Pa.s) to the density $\rho$ (kg/m$^2$), can be determined by directly measuring the behavior of heat transfer by free convection around a thin metal wire placed and fixed in a liquid or semisolid material as described above, i.e., the heat transfer coefficient $\alpha$(W/m$^2$.k) at the surface of the thin metal wire.

Generally, physical quantities can be made less dependent on temperature by dividing them by density. Accordingly, the coefficient of kinematic, viscosity has a relatively low degree of temperature dependence as compared with the coefficient of viscosity which is significantly dependent on temperature, thus making it possible to detect changes in the physical property more accurately and validly.

In this connection, it has been a conventional practice to measure the coefficient of kinamatic viscosity of a material by means of a capillary viscometer. However, since this method is, so to say, a static method, measurement is impossible in systems where the coefficient of kinematic viscosity changes with time. Moreover, the range of measurable values is limited to at most one order of magnitude. Furthermore, in proportion to expected values for the coefficient of kinematic viscosity of a material to be tested, a plurality of capillary viscometers must be provided.

According to the present invention, the temperature difference between a liquid or semisolid material to be tested and a thin metal wire placed therein is used to calculate the heat transfer coefficient at the surface of the thin metal wire and the coefficient of kinematic viscosity of the material in the manner described below. The thin metal wire used for this purpose has a diameter of 0.03 to 2 mm and preferably comprises platinum. If it is desired to insulate the thin metal wire electrically for convenience of operation, it may be coated with a very thin electrically insulating film having a thickness equal to 1/10 or less of the diameter of the thin metal wire.

First of all, when the rate of change of temperature $(\partial \theta / \partial t)$ with respect to time is zero, the heat transfer coefficient $\alpha$ at the surface of the thin metal wire is given by the following equation (2) derived from the analytical solution of Fourier's equation of heat transfer (1) in a cylindrical coordinate system.

$$(\partial \theta / \partial t) = a \nabla^2 \theta \tag{1}$$

$$\alpha = W \cdot d / 4 \Delta \theta \tag{2}$$

where $\theta$ is temperature (°C.), t is time (s), a is thermal diffusivity (m²/s), W is the amount of (w/m²) generated in the thin metal wire, and d is the diameter (m) of the thin metal wire.

Accordingly, if W and d are known, the heat transfer coefficient can be calculated from the temperature difference $\Delta \theta$ according to the above equation (2).

On the other hand, a thin metal wire (e.g., a thin platinum wire) is placed and fixed in distilled water which is known to have a reliable value of the physical property. Then, constant currents (e.g., constant direct currents) having various intensities are passed through the thin platinum wire to measure the temperature difference $\Delta \theta$ between the distilled water and the (heated) thin platinum wire in each case. Thus, there can be obtained an equation relating the Nusselt number Nu (a dimensionless number derived from the heat transfer coefficient) to the Grashof number Gr (a dimensionless number derived from the coefficient of kinematic viscosity), i.e., the following equation (3) generally expressing the phenomenon of heat transfer by free convection.

$$Nu = C_1 Gr^{C_2} \tag{3}$$

where $C_1$ and $C_2$ are constants.

The Nusselt number Nu and the Grashof number Gr are given by the following equations:

$$Nu = \alpha d / \lambda \tag{4}$$

$$Gr = d^3 g \beta \Delta \theta / \nu^2 \tag{5}$$

where $\lambda$ is the heat transfer rate (w/mk), g is the acceleration of gravity (m/s²), $\beta$ is the coefficient of cubic expansion (1/K.), and $\nu$ is the coefficient of kinematic viscosity (m²/s).

Thus, from the above equations (2) to (5), the coefficient of kinematic viscosity $\nu$ of the material being tested is expressed by the following equation:

$$\nu^2 = d^3 g \beta \left( \frac{R_0 (1 + \alpha_w \cdot \theta_w) i^2}{C_1 \pi \lambda d l} \right)^{-\frac{1}{C_2}} \Delta \theta^{1 + \frac{1}{C_2}} \tag{6}$$

where $R_0$ is the electric resistance ($\Omega$) at 0° C. of the thin metal wire (e.g., thin platinum wire) used as sensor, $\theta_w$ is the temperature (°C.) of the thin metal wire, $\alpha_w$ is the temperature coefficient (1/K.) of electric resistance of the thin metal wire, i is the intensity (A) of the electric current flowing through the thin metal wire, and l is the length (m) of the thin metal wire.

In the above equation (6), d, g, $R_0$, $\alpha_w$ and l are always constant and, moreover, changes in $\beta$ and $\lambda$ are negligibly small for gel-like foods as described above. In the result, the coefficient of kinematic viscosity $\nu$ is considered to be a function of i and $\Delta \theta$ alone and can be expressed by the following equation:

$$\nu^2 = C_3 i^{-\frac{2}{C_2}} \Delta \theta^{1 + \frac{1}{C_2}} = f(i, \Delta \theta) \tag{7}$$

where $C_3$ is a constant.

Now, the results of an experiment conducted in order to confirm the accuracy of the $\nu$ value given by the above equation (7) will be described hereinbelow.

EXPERIMENTAL PROCEDURE

A thin platinum wire having a diameter of 0.1 mm and a length of 106 mm ($R_0 = 1.36965 \Omega$, $\alpha_w = 3.8166 \times 10^{-3}$ 1/K.) was fastened within a cylindrical stainless steel container having an internal diameter of 50 mm, as shown in FIG. 1. The sensor so constructed was immersed in distilled water varying in temperature from 4.4° C. to 51.9° C., and the Nussert number and the Grashof number were measured by passing a constant direct current of 0.5–1.0 A through the thin platinum wire. As a result, there was obtained the following regression equation having a high level of significance:

$$Nu = 1.21 \, Gr^{0.221} \tag{8}$$

Thus, from this equation (8), the constants $C_1$ and $C_2$ in the above equation (3) can be determined to be 1.21 and 0.221, respectively.

Next, the sensor was placed in reconstituted skim milk (30° C., pH 6.59) having a total solid content of 10% and a constant direct current of 0.7 A was passed through the thin platinum wire. Immediately after the current began to flow, the temperature of the thin platinum wire reached an equilibrium value of 36.94° C. to give a temperature difference $\Delta \theta$ of 6.94 K. On the other hand, according to conventional procedure, the coefficient of cubic expansion $\beta$ and thermal conductivity $\lambda$ of the skim milk were determined to be $4.32 \times 10^{-4}$ 1/K. and 0.596 w/mk, respectively. From these values, the coefficient $C_3$ in the above equation (7) was determined to be $9.54 \times 10^{-19}$. Then by substituting $\Delta\theta = 6.94$ K., $i = 0.7$ A and $C_2 = 0.221$ into equation (7), the coefficient of kinematic viscosity $\nu$ of the skim milk was calculated at $(1.04 \pm 0.31) \times 10^{-6}$ m$^2$/s. This calculated value was in good agreement with the measured value of $1.368 \times 10^{-6}$ m$^2$/s which was obtained by means of a capillary viscometer.

It may be seen from the above-described relationships that, if the temperature difference $\Delta\theta$ between a thin metal wire used as sensor and a liquid or semisolid sample of a material to be tested is kept constant and if the $\beta$ and $\lambda$ values of the aforesaid sample are determined in advance according to conventional procedure, the coefficient of kinematic viscosity of the sample can be directly obtained from the above equation (7), simply by measuring the intensity $i$ of the electric current flowing through the thin metal wire.

The temperature $\theta_w$ of the thin metal wire can be obtained by measuring the voltage $V$ across the thin metal wire and then calculating the temperature according to the following equation.

$$\theta_w = (V/iR_0 - 1)/\alpha_w \qquad (9)$$

Moreover, even if the value for $C_3$ (i.e., the values for $\beta$ and $\lambda$) is unknown, the relative change $\Gamma^*(-)$ in the coefficient of kinematic viscosity can be obtained because the above equation is rewritten as follows:

$$\nu^* = (i/i_0)^{1/C_2} \qquad (10)$$

where $\Delta\theta$ is constant and $i_0$ represents the initial intensity (A) of electric current flowing through the thin metal wire.

As described above, according to the method of the present invention, a thin metal is placed in a liquid or semisolid material, an electric current is passed through the thin metal wire to heat it in such a way that the temperature difference $\Delta\theta$ between the material and the thin metal wire is kept constant, and the intensity of the electric current is measured, whereby changes in a physical property of the material can be directly detected as changes in the heat transfer coefficient at the surface of the thin metal wire. That is, changes in a physical property of the material can be measured in real time and continuously without causing the internal structure of the material to be mechanically or thermally destroyed to any significant degree.

Accordingly, the method of the present invention using the aforesaid thin metal wire as sensor may be incorporated into automated processes for the manufacture of gel-like foods (such as cheese, yogurt, bean curd, jelly, pudding, etc.) in which changes in kinematic viscosity are important for the quality thereof, whereby parameters (such as coagulation rate) concerning the conversion of these foods from a liquid to a semisolid state can be precisely evaluated with the lapse of time.

In this connection, it has been a conventional practice in the manufacture of such gel-like foods to determine appropriate gelling conditions empirically and use them as indices to the manufacture thereof. In contrast, if a theory similar to that of heat transfer by free convention is applied according to the procedure taught by the present invention, the coefficient of kinematic viscosity as a physical quantity can be calculated from the heat transfer coefficient which is, so to say, a quantity of state. This makes it possible to determine the optimum gelling conditions resting on a scientific basis.

Figure 4:
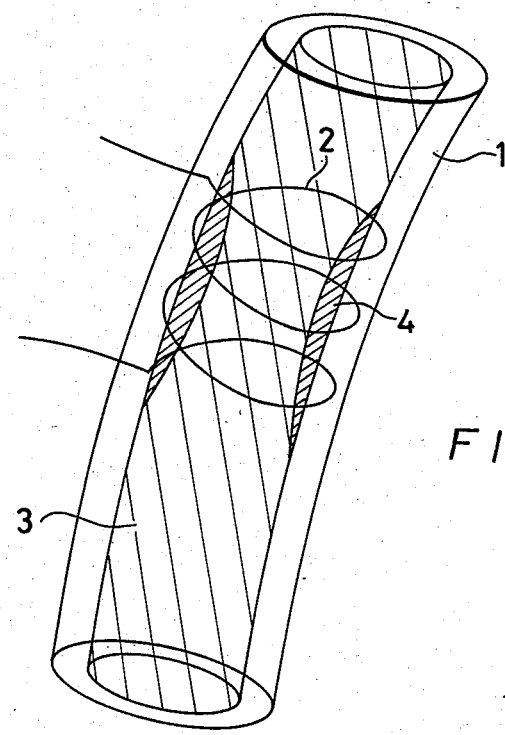
FIGS. 4 and 5 are views showing an embodiment of the present invention for detecting the condition of thrombus formation on the inner surface of an artificial blood vessel.
Figure 5:
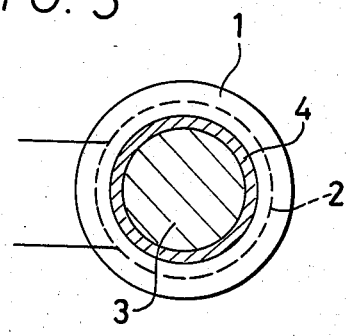

Moreover, according to the method of the present invention, changes in the aforesaid heat transfer coefficient can be used as such to detect changes in a physical property of biological fluids including blood. In one exemplary embodiment, as shown in FIGS. 4 and 5, a thin metal wire (such as a thin platinum wire) 2 is fixed in the wall, or within the bore, of an artificial blood vessel 1. Then, the deposition of "soil" (i.e., the formation of a thrombus) on the inner surface of the blood vessel can be directly observed by measuring changes in the intensity $i$ of the electric current flowing through the thin metal wire according to the method of the present invention. In these figures, reference numerals 3 and 4 indicate blood and a thrombus, respectively. This is based on the fact that the formation of a thrombus on the inner surface of a blood vessel alters the surface condition of the blood vessel, resulting in a change of heat transfer coefficient.

The measurement, whether in vitro or in vivo, can be made in real time and continuously without destroying the material being tested. Thus, the formation of a thrombus on the inner surface of a blood vessel may be observed without autopsying the subject after its death or sacrifice as has been usual in the prior art.

Accordingly, it may be safely said that the method of the present invention is useful in the study and development of artificial blood vessels, artificial hearts and materials therefor.

It may be mentioned in this connection that, in addition to examination by autopsy, an attempt has also been made to detect the formation of a thrombus by implanting an electromagnetic flowmeter surgically in a living body and detecting any thrombus formation on the basis of changes in blood flow rate. However, from a practical point of view, it has been difficult to detect an early stage of thrombus formation because of insufficient detection sensitivity. In contrast, the method of the present invention makes it possible to sensitively detect even such an amount of soil as cannot be recognized with the naked eye, i.e., a deposit of thrombocytes which is observed in a very early stage of thrombus formation.

In addition to the above-described applications, the method of the present invention makes it possible to fractionate fats, oils and butter according to their melting points and to examine the state of fat globules and the like. Furthermore, changes in the internal structure of various liquid and semisolid materials including biological fluids can also be continuously and accurately measured by a simple procedure.

The present invention is further illustrated by the following examples.

EXAMPLE 1

This example illustrates the measurement of changes in viscosity of skim milk during its coagulation process.

Figure 2:
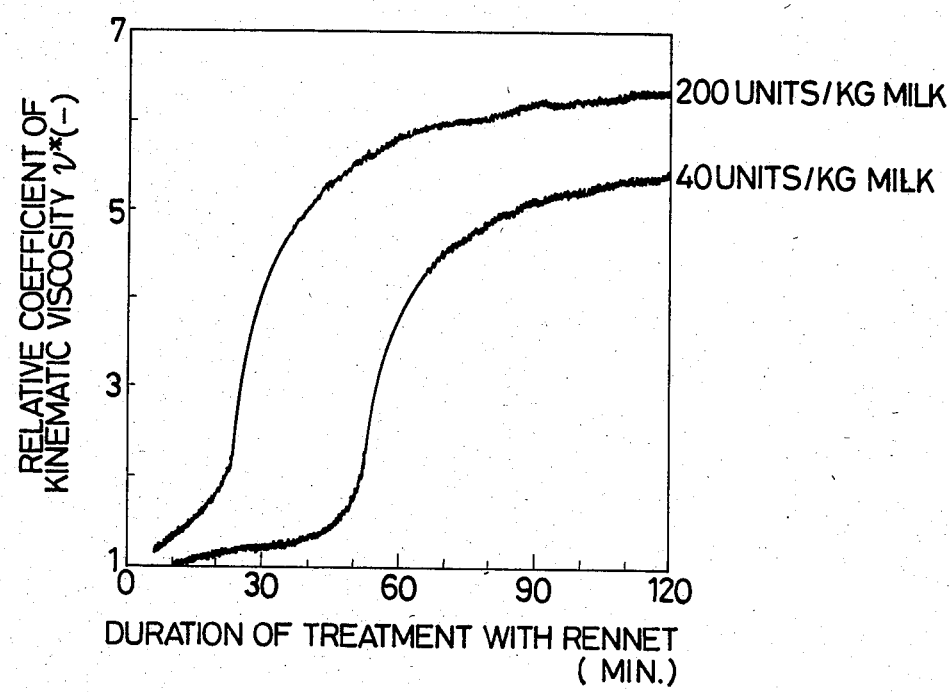
FIG. 2 is a graph showing the relationships between the relative coefficient of kinematic viscosity measured by the method of the present invention and the duration of treatment with rennet.

A platinum wire having a diameter of 0.1 mm and a length of 106 mm ($R_0 = 1.36965\Omega$, $\alpha_w = 3.8166 \times 10^{-3}$ 1/K.) was fastened within a cylindrical stainless steel container having an internal diameter of 50 mm, as shown in FIG. 1. The sensor so constructed was placed and fixed in a sample of reconstituted skim milk having a total solid content of 10%. To this skim milk sample was added 4,000 or 200,000 units/kg of the milk-coagulating enzyme chymosin [EC 3.4.23.4; a preparation having a purity of about 95% was used and one unit (about 17 ng) thereof had the ability to coagulate 10 ml of raw milk (30° C.) in a minute]. In each case, the skim milk sample was allowed to coagulate at 30° C. for 2 hours, during which time the intensity i of the electric current required to keep the temperature difference $\Delta\theta$ between the platinum wire and the skim milk sample at 6.94 K. ($i_0 = 0.7$ A) was measured. Using the measured values, the coefficient of kinematic viscosity of the skim milk being coagulated was calculated from the above equation (10) to examine its change continuously. Thus, as shown in FIG. 2, the coefficient of kinematic viscosity was found to increase by a factor of about 5.5 or about 6.5, respectively.

It may be understood from this example that the method of the present invention neither involves the necessity of deforming the curd by the application of an external force or breaking down the curd, nor brings about the separation of water from the curd due to excessive heating caused by the electric current flowing through the platinum wire, thus permitting accurate and continuous measurement of changes in viscosity of the milk being coagulated.

Figure 3:
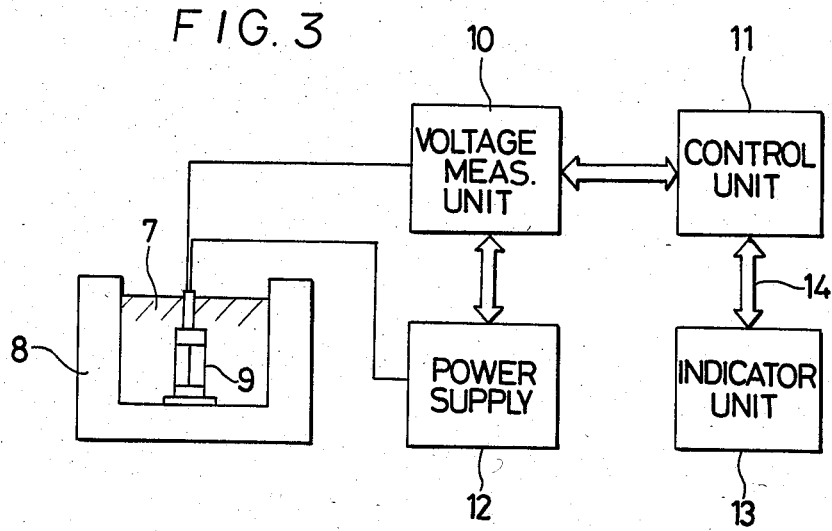
FIG. 3 is a schematic diagram showing a measuring apparatus for use in the present invention.

FIG. 3 is a schematic view of the apparatus used for the above-described measurements. In this figure, the skim milk sample, the thermostatically controlled bath containing it, and the platinum wire used as sensor are indicated at 7, 8 and 9, respectively. Reference numerals 10, 11, 12, 13 and 14 indicate a voltage measuring unit, a control unit, a power supply unit, an indicator unit and an automatic control system, respectively. The aforesaid temperature difference $\Delta\theta$ was obtained from the temperature of the skim milk sample which had been continuously measured with a platinum resistance thermometer and the temperature of the platinum wire (sensor) which had been calculated from the above equation (9). It is to be understood that the measurement of the temperature difference $\Delta\theta$ is not limited to the above-described procedure, but any other procedure may be used for this purpose.

EXAMPLE 2

To raw milk having a total solid content of 12.0±0.4% and a fat content of 3.5±0.1% were added 0.5% by weight of lactic acid bacteria starter (with an acidity of 0.87 and a pH of 4.53) and 0.0035% by weight (about 5,000 units/kg milk) of rennet. While the milk was allowed to coagulate at a temperature of 31° C., the relative coefficient of kinematic viscosity $\nu^*$ of the curd was measured by using the same sensor as used in Example 1 and following the same procedure as described in Example 1. On the other hand, the optimum time for cutting of the curd (i.e., the optimum viscosity of the milk being coagulated) was organoleptically determined by a skilled worker. Thus, the relationship between the relative coefficient of kinematic viscosity measured as above and the optimum time for cutting was examined four times over.

As a result, the values of $\nu^*$ at the organoleptically determined optimum time for cutting of the curd (about 60 minutes after the addition of rennet) were found to be reproducibly equal to about 9.2.

Accordingly, in the process of coagulating milk by the addition of rennet, the method of the present invention may be used to measure the $\nu^*$ value of the milk continuously. Then, by cutting the curd as soon as the $\nu^*$ value increasing gradually from its initial level of 1 has reached 9.2, curd cutting at the optimum time can be achieved without depending on an organoleptic judgment by a skilled worker.

It may be mentioned in this connection that the water content of curd varies significantly according to the time of cutting. For example, the water content of green cheese varies with the time of cutting, as shown in the following table.

TABLE

| Time of cutting (time elapsed after the addition of rennet, minutes) | Water content of green cheese (%) |
| --- | --- |
| 50 | 48.0 |
| 60 | 49.2 |
| 80 | 50.3 |

Generally, if the water content of green cheese is too much, undesired bacteria may grow during ripening or the ripening rate may become excessively high. On the other hand, if the water content is too low, the progress of ripening may be hindered. Since the final quality of cheese will be deteriorated in either case, it is very important for the production of cheese of good and constant quality to detect the optimum time for cutting of curd.

Thus, the method of the present invention makes it possible to produce cheese of good quality consistently. Moreover, if the method of the present invention is incorporated into a process for the manufacture of cheese, the process can be automated by substituting a closed vat of large size for the open-top cheese vat heretofore in use.

EXAMPLE 3

This example illustrates the applicability of the method of the present invention to the detection of the condition of thrombus formation in a blood vessel system. In a simulation experiment involving the process of thrombus formation in an artificial blood vessel system, milk that is empirically known to be capable of replacing blood and an artificial blood vessel comprising a silicone tube were used to measure changes in the amount of coagulated milk deposited on the inner surface of the tube.

As shown in FIGS. 4 and 5, an artificial blood vessel 1 comprised a silicone tube having an internal diameter of 10 mm and a wall thickness of 2 mm, and a platinum wire 2 having a diameter of 0.1 mm and a length of 130 mm was implanted in the wall of the tube to a depth of 0.3 mm from its inner surface. To reconstituted skim milk (36° C.) having a total solid content of 10% was added 0.2% by weight (about 300,000 units/kg milk) of rennet. Immediately after that, the milk being coagulated was made to flow through the aforesaid artificial blood vessel 1 at a flow velocity of about 10 cm/sec. At the same time, an electric current was passed through the aforesaid platinum wire. Thus, the intensity of electric current ($i_0 = 0.6$ A) required to keep the temperature difference $\Delta\theta$ between the milk and the platinum wire at 3° C. showed a decrease of 16.1%.

What is claimed is:

1. A method for measuring changes in a physical property of a liquid or semisolid material which comprises placing a thin metal wire in said material; passing an electric current continuously or intermittently through said thin metal wire in such a way that the temperature difference between said material and said thin metal wire is kept constant; measuring the intensity of said electric current; and calculating the heat transfer coefficient at the surface of said thin metal wire on the basis of the measured intensity of said electric current and thereby detecting changes in a physical property of said material.

2. A method as claimed in claim 1 wherein said semi-solid material is a food having the form of a gel and changes in its coefficient of kinematic viscosity are detected.

3. A method as claimed in claim 1 wherein said liquid material is blood and changes in the condition of thrombus formation in a blood vessel are detected.

4. A method as claimed in claim 1 wherein said thin metal wire is coated with an electrical insulating film.

5. A method as claimed in claim 1 wherein said thin metal wire is a thin platinum wire.

6. A method as claimed in claim 1 wherein said electric current is a direct current.

* * * * *